(12) United States Patent
Tanaka et al.

(10) Patent No.: US 11,703,157 B2
(45) Date of Patent: *Jul. 18, 2023

(54) BRAIDED TUBE

(71) Applicant: Hitachi Metals, Ltd., Tokyo (JP)

(72) Inventors: Kotaro Tanaka, Tokyo (JP); Takanobu Watanabe, Tokyo (JP); Kimika Kudo, Tokyo (JP); Takanori Komuro, Tokyo (JP)

(73) Assignee: PROTERIAL, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 17/035,240

(22) Filed: Sep. 28, 2020

(65) Prior Publication Data

US 2021/0095796 A1 Apr. 1, 2021

(30) Foreign Application Priority Data

Sep. 30, 2019 (JP) .................................. 2019-179829

(51) Int. Cl.
*F16L 11/08* (2006.01)

(52) U.S. Cl.
CPC .................. *F16L 11/085* (2013.01)

(58) Field of Classification Search
CPC .................................................. F16L 11/085
USPC ........................................................ 138/125
See application file for complete search history.

(56) References Cited

U.S. PATENT DOCUMENTS

| | | | | |
|---|---|---|---|---|
| 3,540,486 A | * | 11/1970 | Flounders | F16L 33/207 285/256 |
| 3,722,550 A | * | 3/1973 | Matthews | F16L 11/085 138/137 |
| 4,330,017 A | * | 5/1982 | Satoh | F16L 11/086 138/126 |
| 5,246,426 A | | 9/1993 | Lewis et al. | |
| 5,538,513 A | | 7/1996 | Okajima | |
| 5,613,523 A | * | 3/1997 | Klawuhn | F16L 11/085 138/126 |

(Continued)

FOREIGN PATENT DOCUMENTS

| | | |
|---|---|---|
| JP | H06-134034 A | 5/1994 |
| JP | H07-507945 A | 9/1995 |

(Continued)

OTHER PUBLICATIONS

Office Action issued in corresponding Japanese Patent Application No. 2019-179829 dated Oct. 4, 2022; 6 pages.

(Continued)

*Primary Examiner* — Craig M Schneider
*Assistant Examiner* — David R Deal
(74) *Attorney, Agent, or Firm* — Thomas W. Cole; Calderon Safran & Cole P.C.

(57) ABSTRACT

A braided tube includes a hollow cylindrical inner resin layer made of thermoplastic polyurethane resin, a braided wire including braided strands made of nylon and being provided over a periphery of the inner resin layer, and an outer resin layer made of thermoplastic polyurethane resin and being provided to cover peripheries of the inner resin layer and the braided wire. A width of a void formed around the strand of the braided wire in a cross section perpendicular to a tube longitudinal direction is 30 µm or less.

5 Claims, 4 Drawing Sheets

(56) References Cited

U.S. PATENT DOCUMENTS

| | | | | |
|---|---|---|---|---|
| 5,622,210 | A | * | 4/1997 | Crisman ................ F16L 11/115 |
| | | | | 138/104 |
| 5,690,146 | A | * | 11/1997 | Stammen ............... F16L 11/045 |
| | | | | 116/208 |
| 6,109,306 | A | | 8/2000 | Kleinert |
| 6,179,008 | B1 | * | 1/2001 | Kawazura ................ B32B 7/12 |
| | | | | 138/125 |
| D499,465 | S | * | 12/2004 | Paul, III ............... F16L 33/207 |
| | | | | D23/266 |
| 8,357,141 | B2 | | 1/2013 | Mukai et al. |
| 9,857,001 | B2 | * | 1/2018 | Manas-Zloczower ........................ |
| | | | | F16L 11/04 |
| 10,458,573 | B2 | * | 10/2019 | Burrowes ................. B32B 1/08 |
| 10,695,531 | B2 | | 6/2020 | Suzuki |
| 2004/0134555 | A1 | * | 7/2004 | Powell ..................... B32B 7/12 |
| | | | | 138/141 |
| 2005/0199308 | A1 | * | 9/2005 | Swails .................. F16L 33/227 |
| | | | | 138/109 |
| 2007/0265595 | A1 | | 11/2007 | Miyamoto et al. |
| 2009/0088727 | A1 | | 4/2009 | Mukai et al. |
| 2010/0055367 | A1 | * | 3/2010 | Ohigawa ................... B32B 7/12 |
| | | | | 428/36.91 |
| 2014/0326355 | A1 | * | 11/2014 | Nonaka ................ F16L 11/086 |
| | | | | 138/126 |
| 2018/0296795 | A1 | | 10/2018 | Suzuki |

FOREIGN PATENT DOCUMENTS

| | | |
|---|---|---|
| JP | 2000-035167 A | 2/2000 |
| JP | 2006-110224 A | 4/2006 |
| JP | 2007-301360 A | 11/2007 |
| JP | 2008-086340 A | 4/2008 |
| WO | 2017110757 A1 | 6/2017 |

OTHER PUBLICATIONS

Office Action—Decision of Refusal issued in corresponding Japanese Patent Application No. 2019-179829 dated Mar. 28, 2023; 6 pages.

Office Action—Decision of Dismissal of Amendment issued in corresponding Japanese Patent Application No. 2019-179829 dated Mar. 28, 2023; 4 pages.

Office Action issued in corresponding Japanese Patent Application No. 2019-179829 dated Jan. 17, 2023; 8 pages.

* cited by examiner

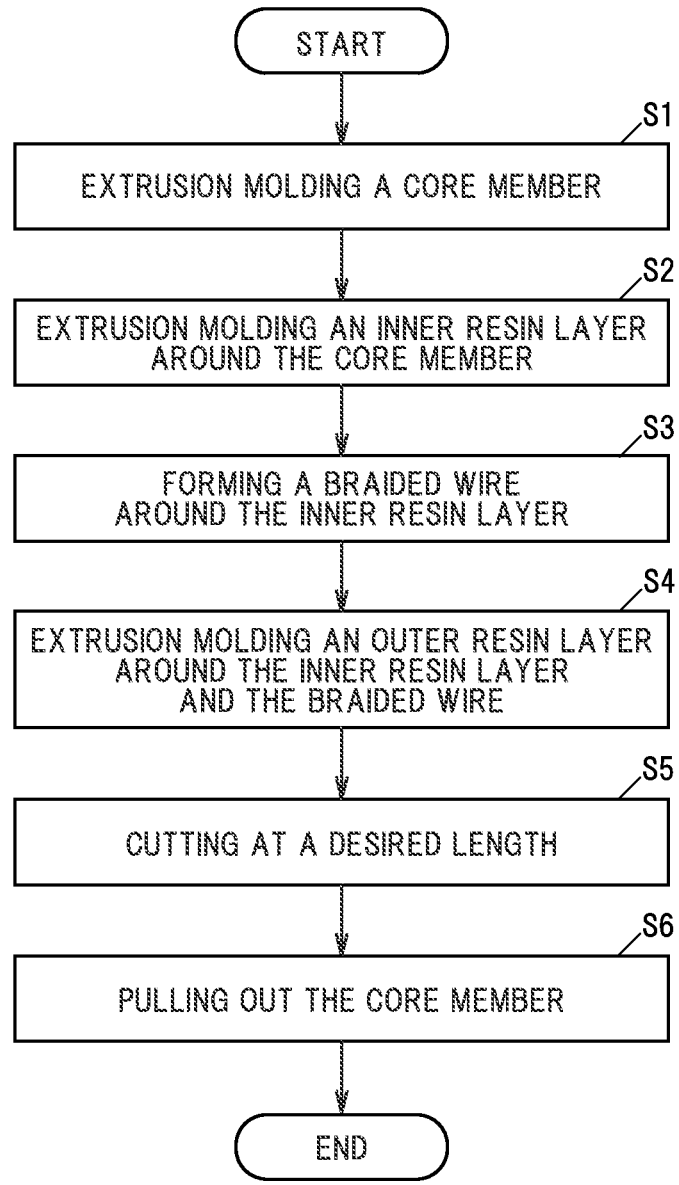

BRAIDED TUBE

CROSS-REFERENCE TO RELATED APPLICATION

The present application is based on Japanese Patent Application No. 2019-179829 filed on Sep. 30, 2019, the entire contents of which are incorporated herein by reference.

BACKGROUND OF THE INVENTION

1. Field of the Invention

The present invention relates to a braided tube.

2. Description of the Related Art

For example, in percutaneous coronary angioplasty (PTCA) and percutaneous angioplasty (PTA), a braided tube has been used as a pressure resistant tube used for an indeflator for inflating and deflating a dilatation balloon catheter, or the like.

As the braided tube, it has been known a braided tube with a structure in that a braided wire including braided strands made of nylon is embedded in a tube made of thermoplastic polyurethane resin (TPU).

As prior art document information related to the invention of this application, there is JP2008-86340A.
[Patent Document 1] JP2008-86340A

SUMMARY OF THE INVENTION

In the above-mentioned indeflator, a liquid such as a contrast agent flows through the braided tube. If air bubbles are mixed in this liquid, a desired operation may not be achieved. Therefore, the braided tube is required to have high transparency in such a manner that the transparent liquid flowing through the inside of the braided tube and the outer shape of the bubbles contained in the liquid can be visually observed.

Therefore, it is an object of the present invention to provide a braided tube with high transparency.

For the purpose of solving the above-described problems, the present invention provides a braided tube comprising:

a hollow cylindrical inner resin layer comprising thermoplastic polyurethane resin;

a braided wire including braided strands comprising nylon and being provided over a periphery of the inner resin layer; and an outer resin layer comprising thermoplastic polyurethane resin and being provided to cover peripheries of the inner resin layer and the braided wire, wherein a width of a void formed around the strand of the braided wire in a cross section perpendicular to a tube longitudinal direction is 30 µm or less.

Points of the Invention

According to the present invention, it is possible to provide a braided tube with high transparency.

BRIEF DESCRIPTION OF THE DRAWINGS

FIG. 5 is a flow chart showing a process for manufacturing the braided tube in FIG. 1.

DETAILED DESCRIPTION OF THE PREFERRED EMBODIMENT

Embodiment

Hereinafter, an embodiment of the present invention will be described with reference to the appended drawings.

(Explanation of an Indeflator Using a Braided Tube)

Figure 1:
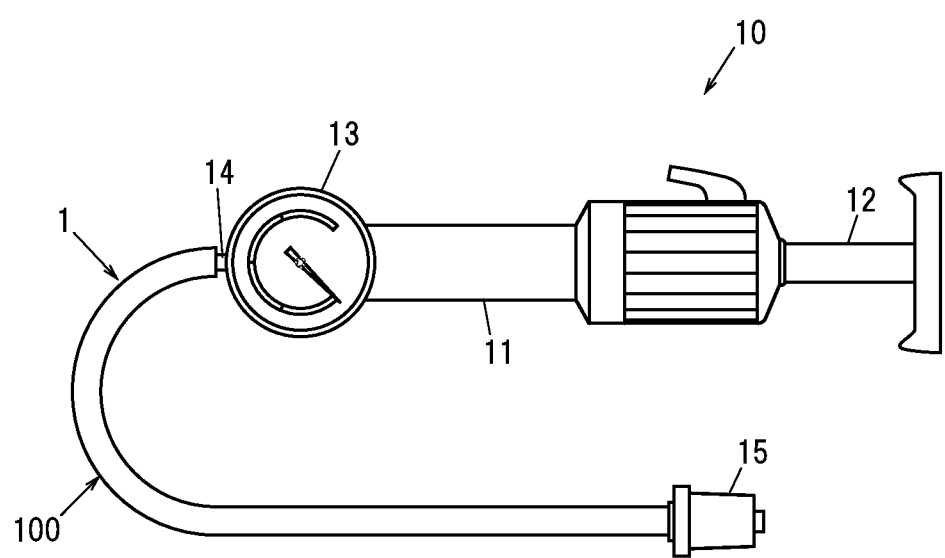
FIG. 1 is a plan view of an indeflator using a braided tube according to an embodiment of the present invention.

FIG. 1 is a plan view of an indeflator 10 using a braided tube 1 according to an embodiment of the present invention. The indeflator 10 is configured for inflating and deflating a dilatation balloon catheter in percutaneous coronary angioplasty (PTCA) or percutaneous angioplasty (PTA).

As shown in FIG. 1, the indeflator 10 is a so-called plunger pump (or piston pump) that delivers or sucks a working fluid such as a contrast agent, and includes a cylinder 11, a plunger (or piston) 12, and a pressure gauge 13 for detecting the pressure of the working fluid inside the cylinder 11.

In the indeflator 10, one end of the braided tube 1 is connected to a liquid inlet/outlet 14 for discharging or sucking the working fluid. The other end of the braided tube 1 is provided with a connector (luer connector) 15. In the present embodiment, a dilatation balloon catheter (not shown) is connected to the connector 15.

In the indeflator 10, the plunger 12 is moved back and forth to pressurize and depressurize the working fluid to inflate and deflate (expand and contract) the dilatation balloon catheter. At this time, for example, if air bubbles are mixed in the braided tube 1, the working fluid may not be pressurized or depressurized as intended, and the dilatation balloon catheter may perform an unintended operation. In addition, since a transparent liquid may be used as the working fluid, the braided tube 1 is required to have high transparency in such a manner that the transparent liquid flowing through the inside of the braided tube 1 and the outer shape of the bubbles contained in the liquid can be visually observed. Further, when the working fluid is pressurized, if a part of the braided tube 1 is expanded, the working fluid will not be pressurized as intended and the dilatation balloon catheter may perform an unintended operation. Therefore, the braided tube 1 is required to have high pressure resistance.

(Explanation of the Braided Tube 1)

Figure 2A:
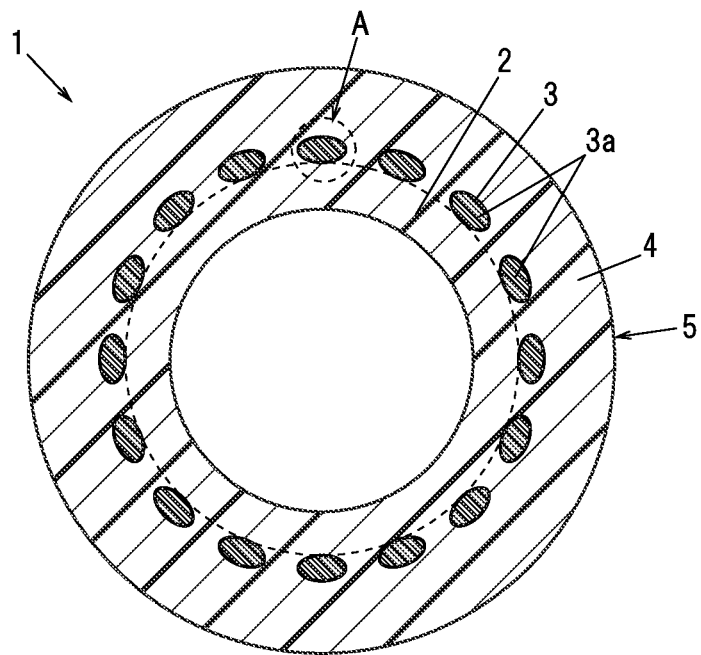
FIG. 2A is a cross-sectional view showing a cross section of a braided tube in a direction perpendicular to a tube longitudinal direction.
Figure 2B:
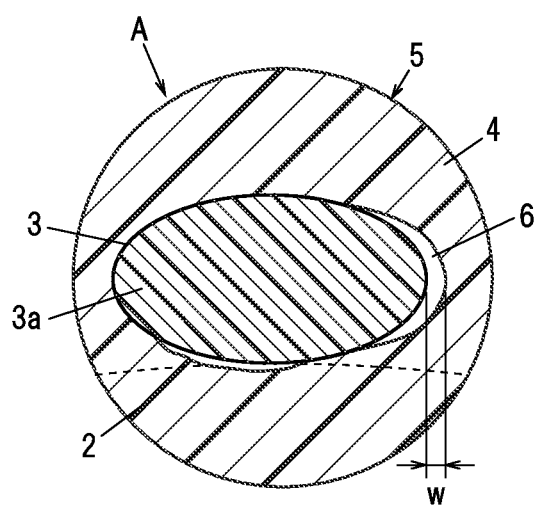
FIG. 2B is an enlarged view of a part A of the braided tube in FIG. 2A.
Figure 3:
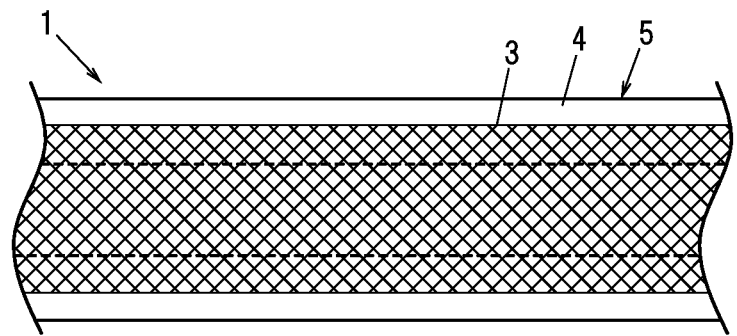
FIG. 3 is a side view of a cross section of the braided tube in FIG. 1.

FIG. 2A is a cross-sectional view showing a cross section of the braided tube 1 in a direction perpendicular to a tube longitudinal direction. FIG. 2B is an enlarged view of a part A of the braided tube 1 in FIG. 2A. FIG. 3 is a side view of a cross section of the braided tube 1 in FIG. 1. The braided tube 1 in the present embodiment is configured to be used for e.g. the aforementioned indeflator, and generally used for the medical application.

As shown in FIGS. 2A, 2B and 3, the braided tube 1 includes a hollow cylindrical inner resin layer and 2, a braided wire 3 formed by braiding strands (elemental wires) 3a over a periphery of the inner resin layer 2, and an outer resin layer 4 provided so as to cover peripheries of the inner resin layer 2 and the braided wire 3.

The inner resin layer 2 and the outer resin layer 4 are made of a material that transmits visible light. In the present embodiment, the inner resin layer 2 and the outer resin layer 4 are made of thermoplastic polyurethane resin (TPU). Hereinafter, the inner resin layer 2 and the outer resin layer 4 are collectively referred to as a resin layer 5. In the present embodiment, an inner diameter of the resin layer 5 (an inner diameter of the inner resin layer 2) is 1.70 mm or more and 1.90 mm or less, and an outer diameter of the resin layer 5 (an outer diameter of the outer resin layer 4) is 3.50 mm or more and 3.70 mm or less. An entire thickness of the resin layer 5 is 0.80 mm or more and 1.00 mm or less.

The outer resin layer 4 is configured to enter into gaps between the strands 3a of the braided wire 3 in such a manner that the outer resin layer 4 is in contact with the peripheries of the strands 3a without any gap as close as possible (it will be described later in more detail). Further, the outer resin layer 4 and the inner resin layer 2 are fused and integrated by heat generated when the outer resin layer 4 is molded. A melting point of a resin constituting the outer resin layer 4 is preferably higher than a melting point of a resin constituting the inner resin layer 2 such that the outer resin layer 4 and the inner resin layer 2 are fused and integrated by the heat generated when the outer resin layer 4 is molded.

The strand 3a of the braided wire 3 is made of nylon. Further, as the strand 3a of the braided wire 3, it is preferable to use a non-colored material in order to increase the transparency of the braided tube 1. Non-colored nylon is a transparent material that transmits visible light. In FIGS. 2A and 2B, a cross-sectional shape of the strands 3a is elliptical, but this is because that the strands 3a are arranged along a direction which is inclined with the tube longitudinal direction, and the cross-sectional shape of the strand 3a in the direction perpendicular to the tube longitudinal direction is circular.

An outer diameter of the strand 3a of the braided wire 3 is preferably 0.20 mm or less. This is because if the strand 3a of the braided wire 3 is too thick, it may be difficult to visually recognize the liquid flowing through the braided tube 1 and the bubbles contained in the liquid (that is, the transparency may be reduced). By making the outer diameter of the strand 3a as thin as 0.20 mm or less, the braided wire 3 becomes inconspicuous, and the transparent liquid flowing through the braided tube 1 and the bubbles contained in the liquid are easily visible. In the present embodiment, the strand 3a having an outer diameter of 0.15 mm is used. If the strand 3a is too thin (fine), the pressure resistance may decrease. Therefore, the outer diameter of the strand 3a is preferably 0.10 mm or more.

The present inventors have studied to increase the transparency of the braided tube 1. Then, the present inventors found that, for example, when a strong pulling force is applied to the braided tube 1 along the tube longitudinal direction, the braided wire 3 becomes white in noticeable state, so that it becomes difficult to visually recognize the transparent liquid flowing through the braided tube 1 and the bubbles contained in the liquid. As a result of further study, the present inventors found that the braided wire 3 becomes white and noticeable since the strand 3a of the braided wire 3 is peeled off from the resin layer 5 around the braided wire 3 and a void is formed around the strand 3a.

Therefore, in the braided tube 1 according to the present embodiment, a width w of a void (gap) 6 formed around the strand 3a of the braided wire 3 is 30 μm or less in the cross section perpendicular to the tube longitudinal direction. The width w of the void 6 is the shortest distance between an outer surface of the strand 3a and the resin layer 5 (the inner resin layer 2 or the outer resin layer 4) that face each other across the void 6 in the cross section perpendicular to the tube longitudinal direction. By reducing the width w of the void 6 to 30 μm or less, the braided wire 3 becomes less noticeable and the transparency of the braided tube 1 is improved. As a result, the transparent liquid flowing inside the braided tube 1 and the outer shape of the bubbles contained in the liquid can be easily visually recognized. In addition, in order to further increase the transparency of the braided tube 1, it is more desirable that the width w of the void 6 be 25 μm or less.

Also, for further increasing the transparency of the braided tube 1, it is more desirable to reduce a proportion of voids 6 that are present at the periphery of the strand 3a, and to increase a proportion of close contact between the strand 3a and the resin layer 5 as small as possible. Specifically, it is desirable that a ratio of an outer peripheral length of the strand 3a facing the void 6 to an outer peripheral length of the entire strands 3a is 60% or less in the cross section in the direction perpendicular to the tube longitudinal direction. In other words, it is desirable that the ratio of the outer peripheral length of the strand 3a in close contact with the resin layer 5 to the outer peripheral length of the entire strands 3a is 40% or more in the cross section perpendicular to the tube longitudinal direction.

Figure 4:
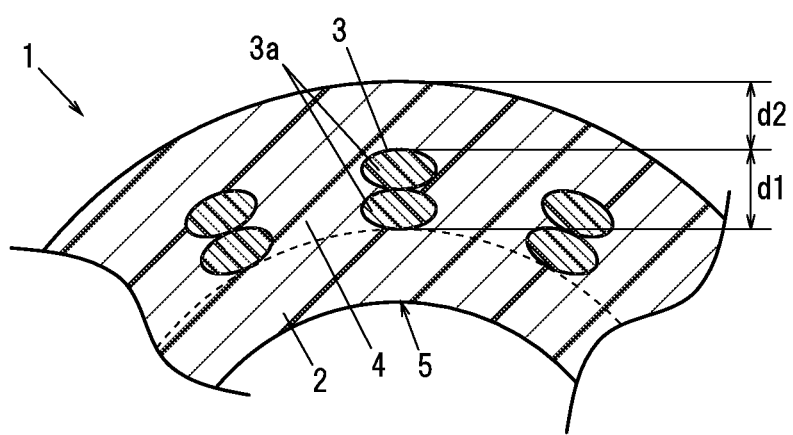
FIG. 4 is an enlarged view of a cross section of the braided tube in FIG. 1 at a point where strands of the braided wire are overlapping in a radial direction.

When the outer resin layer 4 is made thinner, irregularities (unevenness) due to the presence/absence of the strand 3a of the braided wire 3 are transferred to the outer surface of the outer resin layer 4, irregularities (unevenness) will occur at the outer surface of the outer resin layer 4 so that the transparency of the braided tube 1 transparency may decrease. Therefore, the thickness of the outer resin layer 4 radially outward of the braided wire 3 is preferably two or more times of the outer diameter of the strand 3a (not less than a thickness d1 of the braided wire 3). More specifically, as shown in FIG. 4, since the braided wire 3 is formed by braiding a plurality of strands 3a, there is one or more positions where the two strands 3a overlap in a tube radial direction. In this position, a thickness d2 of the outer resin layer 4 positioned radially outward the braided wire 3 is not less than the thickness d1 of the braided wire 3. In the present embodiment, the thickness d2 of the outer resin layer 4 positioned radially outward the braided wire 3 is 0.3 mm or more. Still further, the thickness d1 of the outer resin layer 4 positioned radially outward the braided wire 3 is preferably not less than a thickness of the inner resin layer 2 positioned radially inward the braided wire 3.

Further, in order to increase the pressure resistance of the braided tube 1, it is desired that the inner peripheral surface and the outer peripheral surface of the resin layer 5 have a high degree of concentricity (coaxiality). This is because if the concentricity is low, the resin layer 5 will be partially thin and a thin portion will be deformed (expanded) when pressure is applied to the working fluid. More specifically, the concentricity of the inner and outer peripheral surfaces of the resin layer 5 in a cross section perpendicular to the tube longitudinal direction, i.e., a distance between a center of the inner peripheral surface of the inner resin layer 2 and a center of the outer peripheral surface of the outer resin layer 4 is preferably 0.08 mm or less.

Furthermore, in order to increase the pressure resistance of the braided tube 1, the thickness of the braided tube 1 (the entire thickness of the inner resin layer 2, the braided wire 3, and the outer resin layer 4) is desired to be as homogeneous as possible. Specifically, a value obtained by subtracting the minimum value of the wall thickness of the braided tube 1 from the maximum value of the wall thickness of the braided tube 1 is preferably not more than 0.16 mm.

(Method for Manufacturing the Braided Tube 1)

FIG. 5 is a flow chart showing a process for manufacturing the braided tube 1 in FIG. 1. As shown in FIG. 5, when the braided tube 1 is manufactured, firstly a core member is formed by extrusion molding at step S1. The core member is provided at a center when the inner resin layer 2 is formed by extrusion molding, and removed at later stage (step S6), so as to form a hollow portion for passing the working fluid therethrough. The core member is formed to have a solid linear shape with a circular cross section. In the present embodiment, the core member is made of polyethylene.

Thereafter, at step S2, the inner resin layer 2 is formed around the core member by extrusion molding. At this time, it is preferable that the inner resin layer 2 is formed by so-called tube extrusion so as to facilitate the pulling off of the core member. Thereafter, at step S3, the braided wire 3 is formed by braiding the strands 3a around the inner resin layer 2.

Thereafter, at step S4, the outer resin layer 4 is formed around the inner resin layer 2 and the braided wire 3 by extrusion molding. By setting the conditions of pressure, temperature and the like for performing the extrusion molding of the outer resin layer 4, it is possible to make the resin enter into gaps between the strands 3a of the braided wire 3 and closely contact with the strands 3a, thereby to remarkably reduce the void 6 around the strand 3a (to reduce the width w of the void 6 to be 30 μm or less). In the meantime, it is possible to fuse the inner resin layer 2 and the outer resin layer 4 together in such a manner that the inner resin layer 2 and the outer resin layer 4 are closely in contact with each other and integrated. Here, if the strands 3a of the braided wire 3 is melted at the time of molding the outer resin layer 4, the pressure resistance of the braided tube 1 will deteriorate. Therefore, it is preferable that the outer resin layer 4 is formed by extrusion molding at the temperature to the extent that the strands 3a will not be melted.

Thereafter, at step S5, a linear member obtained at the step S4, namely, the linear member including the inner resin layer 2, the braided wire 3, and the outer resin layer 4 provided around the core member is cut at a desired length (e.g. 30 cm or more and 1 m or less). Thereafter, at step S6, the core member is pulled and removed from the cut linear member to provide the braided tube 1 as shown in FIG. 2.

Operation and Effect of the Embodiment

As described above, the braided tube 1 according to the present embodiment is configured in such a manner that the width w of the void 6 formed around the strand 3a of the braided wire 3 in the cross section perpendicular to the tube longitudinal direction is configured to be 30 μm or less.

By reducing the void 6 formed around the strand 3a of the braided wire 3, the braided wire 3 becomes less noticeable and the transparency of the braided tube 1 is improved. As a result, the transparent liquid flowing inside the braided tube 1 and the outer shape of the bubbles contained in the liquid can be easily visually recognized. Further, the adhesion (close contact) between the strands 3a and the resin layer 5 is improved, so that the shape of the resin layer 5 can be maintained by the braided wire 3, so that it will become hard for the braided tube 1 to lose the cross-sectional shape.

SUMMARY OF THE EMBODIMENT

Next, the technical ideas grasped from the above-described embodiments will be described with the aid of the reference characters and the like in the embodiments. It should be noted, however, that each of the reference characters and the like in the following descriptions is not to be construed as limiting the elements in the appended claims to the members and the like specifically shown in the embodiments.

[1] A braided tube (1) comprising: a hollow cylindrical inner resin layer (2) comprising thermoplastic polyurethane resin; a braided wire (3) including braided strands (3a) comprising nylon and being provided over a periphery of the inner resin layer (2); and an outer resin layer (4) comprising thermoplastic polyurethane resin and being provided to cover peripheries of the inner resin layer (2) and the braided wire (3), wherein a width of a void (6) formed around the strand (3a) of the braided wire (3) in a cross section perpendicular to a tube longitudinal direction is 30 μm or less.

[2] The braided tube (1) according to [1], wherein a ratio of an outer peripheral length of the strand (3a) facing the void (6) to an outer peripheral length of the entire strands (3a) is 60% or less in the cross section perpendicular to the tube longitudinal direction.

[3] The braided tube (1) according to [1] or [2], wherein an outer diameter of the strand (3a) of the braided wire (3) is 0.20 mm or less.

[4] The braided tube (1) according to any one of [1] to [3], wherein a thickness of the outer resin layer (4) positioned radially outward the braided wire (3) is not less than a thickness of the inner resin layer (2) positioned radially inward the braided wire (3).

[5] The braided tube (1) according to any one of [1] to [4], wherein a value obtained by subtracting a minimum value of an entire wall thickness of the inner resin layer (2), the braided wire (3) and the outer resin layer (4) from a maximum value of the entire wall thickness is not more than 0.16 mm.

[6] The braided tube (1) according to any one of [1] to [5], wherein a distance between a center of an inner peripheral surface of the inner resin layer (2) and a center of an outer peripheral surface of the outer resin layer (4) in the cross section perpendicular to the tube longitudinal direction is 0.08 mm or less.

Although the embodiments of the present invention have been described above, the embodiments described above do not limit the invention according to the claims. Further, it should be noted that not all of the combinations of features described in the embodiments are essential to the means for solving the problems of the invention.

The present invention can be appropriately modified and implemented without departing from the spirit of the present invention. For example, in the above embodiment, the braided tube 1 to be used for the indeflator 10 is described, the application use of the braided tube 1 is not limited thereto.

Although the invention has been described with respect to the specific embodiments for complete and clear disclosure, the appended claims are not to be thus limited but are to be construed as embodying all modifications and alternative constructions that may occur to one skilled in the art which fairly fall within the basic teaching herein set forth.

What is claimed is:

1. A braided tube, comprising:
a hollow cylindrical inner resin layer comprising transparent thermoplastic polyurethane resin;
a braided wire including braided strands comprising non-colored nylon and being provided over a periphery of the inner resin layer; and
an outer resin layer comprising transparent thermoplastic polyurethane resin that is fused over peripheries of the inner resin layer and the braided wire,
wherein a melting point of the resin constituting the outer resin layer is higher than the melting point of the resin constituting the hollow cylindrical inner resin layer such that the outer resin layer and inner resin layer are fused and integrated by the heat generated when the outer resin layer is molded, and wherein the outer resin layer is configured to enter into gaps between the braided strands to minimize gaps in the interface between the braided strands and the outer resin layer and to increase transparency.

2. The braided tube according to claim 1, wherein an outer diameter of each strand of the braided wire is 0.20 mm or less.

3. The braided tube according to claim 1, wherein a thickness of the outer resin layer positioned radially outward the braided wire is not less than a thickness of the inner resin layer positioned radially inward the braided wire.

4. The braided tube according to claim 1, wherein a value obtained by subtracting a minimum value of an entire wall thickness of the inner resin layer, the braided wire and the outer resin layer from a maximum value of the entire wall thickness is not more than 0.16 mm.

5. The braided tube according to claim 1, wherein a distance between a center of an inner peripheral surface of the inner resin layer and a center of an outer peripheral surface of the outer resin layer in the cross section perpendicular to the tube longitudinal direction is 0.08 mm or less.

* * * * *